(12) United States Patent
Beckham

(10) Patent No.: US 9,545,325 B2
(45) Date of Patent: Jan. 17, 2017

(54) MEDICAL DEVICE DELIVERY CONTROL MECHANISM

(71) Applicant: Covidien LP, Mansfield, MA (US)

(72) Inventor: D. Scott Beckham, Costa Mesa, CA (US)

(73) Assignee: Covidien LP, Mansfield, MA (US)

( * ) Notice: Subject to any disclaimer, the term of this patent is extended or adjusted under 35 U.S.C. 154(b) by 596 days.

(21) Appl. No.: 13/961,922

(22) Filed: Aug. 8, 2013

(65) Prior Publication Data

US 2015/0045871 A1   Feb. 12, 2015

(51) Int. Cl.
*A61F 2/06*       (2013.01)
*A61F 2/966*      (2013.01)
*A61F 2/95*       (2013.01)

(52) U.S. Cl.
CPC ........ *A61F 2/966* (2013.01); *A61F 2002/9517* (2013.01); *A61F 2002/9665* (2013.01)

(58) Field of Classification Search
CPC ............ A61F 2002/9517; A61F 2/2427; A61F 2/2436; A61F 2/954; A61F 2/962; A61F 2/966; A61F 2002/011; A61F 2002/9528; A61F 2002/9534; A61M 25/0637; A61C 7/02; A61C 7/14; A61C 7/12
USPC  623/1.11, 1.12, 1.23, 2.11; 433/22; 606/200
See application file for complete search history.

(56) References Cited

U.S. PATENT DOCUMENTS

| | | |
|---|---|---|
| 4,129,128 A | 12/1978 | McFarlane |
| 4,161,177 A | 7/1979 | Fuchs |
| 4,224,937 A | 9/1980 | Gordon |
| 5,449,372 A | 9/1995 | Schmaltz et al. |
| 6,491,681 B1 | 12/2002 | Kunis et al. |
| 6,673,042 B1 | 1/2004 | Samson et al. |
| 6,800,085 B2 | 10/2004 | Selmon et al. |
| 7,594,910 B2 | 9/2009 | Butts et al. |
| 7,803,150 B2 | 9/2010 | Chang et al. |
| 7,951,092 B2 | 5/2011 | Jones et al. |
| 8,100,958 B2 | 1/2012 | Fischer et al. |
| 8,317,816 B2 | 11/2012 | Becker |
| 2005/0149160 A1* | 7/2005 | McFerran ................ A61F 2/95 623/1.11 |
| 2009/0012429 A1 | 1/2009 | Heuser |
| 2009/0270877 A1 | 10/2009 | Johnson et al. |

(Continued)

FOREIGN PATENT DOCUMENTS

GB            245948 A      1/1926
JP         2008-253793     10/2008

(Continued)

OTHER PUBLICATIONS

Priestley, et al., "First clinical experience with a new flexible low profile metallic stent and delivery system", European Heart Journal, 1996.

*Primary Examiner* — Melanie Tyson
*Assistant Examiner* — Majid Jamialahmadi
(74) *Attorney, Agent, or Firm* — Mark J. Kertz, Esq.

(57) ABSTRACT

Apparatuses and methods for controlling a medical device delivery assembly are provided. The apparatus can comprise a first engagement device and a coupling mechanism. The first engagement device can be used to engage a first component. The coupling mechanism can have a port and at least one wing. The at least one wing can be disposed adjacent to the port and be configured to facilitate interconnection of the first engagement device with the coupling mechanism.

9 Claims, 13 Drawing Sheets

(56) References Cited

U.S. PATENT DOCUMENTS

| | | | |
|---|---|---|---|
| 2010/0004730 A1* | 1/2010 | Benjamin | A61F 2/95 623/1.11 |
| 2010/0148974 A1* | 6/2010 | Yang | G08B 17/10 340/628 |
| 2010/0279244 A1* | 11/2010 | Nicholson | A61C 7/02 433/4 |
| 2011/0125133 A1 | 5/2011 | Aggerholm et al. | |
| 2011/0270371 A1 | 11/2011 | Argentine | |
| 2012/0226341 A1 | 9/2012 | Schreck et al. | |

FOREIGN PATENT DOCUMENTS

| | | |
|---|---|---|
| WO | WO-92/07610 | 5/1992 |
| WO | WO-2006/093976 | 9/2006 |

\* cited by examiner

MEDICAL DEVICE DELIVERY CONTROL MECHANISM

BACKGROUND

Field of the Inventions

The disclosure relates to medical device delivery systems, and more specifically, to a medical device delivery control mechanisms.

Description of the Related Art

Walls of the vasculature, particularly arterial walls, may develop areas of pathological dilatation called aneurysms. As is well known, aneurysms have thin, weak walls that are prone to rupturing. Aneurysms can be the result of the vessel wall being weakened by disease, injury, or a congenital abnormality. Aneurysms could be found in different parts of the body, and the most common are abdominal aortic aneurysms and brain or cerebral aneurysms in the neurovasculature. When the weakened wall of an aneurysm ruptures, it can result in death, especially if it is a cerebral aneurysm that ruptures.

Aneurysms are generally treated by excluding the weakened part of the vessel from the arterial circulation. For treating a cerebral aneurysm, such reinforcement is done in many ways including: (i) surgical clipping, where a metal clip is secured around the base of the aneurysm; (ii) packing the aneurysm with small, flexible wire coils (micro-coils); (iii) using embolic materials to "fill" an aneurysm; (iv) using detachable balloons or coils to occlude the parent vessel that supplies the aneurysm; and (v) intravascular stenting.

Intravascular stents are well known in the medical arts for the treatment of vascular stenoses or aneurysms. Stents are prostheses that expand radially or otherwise within a vessel or lumen to provide support against the collapse of the vessel. Methods for delivering these intravascular stents are also well known.

In conventional methods of introducing a compressed stent into a vessel and positioning it within in an area of stenosis or an aneurysm, a guiding catheter having a distal tip is percutaneously introduced into the vascular system of a patient. The guiding catheter is advanced within the vessel until its distal tip is proximate the stenosis or aneurysm. A guidewire positioned within an inner lumen of a second, inner catheter and the inner catheter are advanced through the distal end of the guiding catheter. The guidewire is then advanced out of the distal end of the guiding catheter into the vessel until the distal portion of the guidewire carrying the compressed stent is positioned at the point of the lesion within the vessel. Once the compressed stent is located at the lesion, the stent may be released and expanded so that it supports the vessel.

SUMMARY

At least one aspect of the disclosure provides methods and apparatuses for delivering a medical device, such as a filter, an occluding device, or other devices (e.g., stent or stents) in the body. The device can easily conform to the shape of the tortuous vessels of the vasculature. The device can be used in a variety of applications. For example, in some embodiments, the device can direct the blood flow within a vessel away from an aneurysm. Additionally, the device can allow adequate blood flow to be provided to adjacent structures to allow those structures, whether they are branch vessels or oxygen demanding tissues, not to be deprived of the necessary blood flow.

The delivery of a medical device to a treatment site within the vessel of a patient requires substantial precision. Generally, during the implantation process, a medical device is passed through a vessel to a treatment location. For example, a stent can be expanded at the treatment location, often by allowing a first end of the stent to expand and thereafter slowly expanding the remainder of the stent until the entire stent has been expanded. The process of expanding a stent at a proper treatment location requires the coordination of the motion of several components of a medical device delivery assembly. In some embodiments, the stent must be recaptured, withdrawn, rotated or resheathed back into a catheter after the stent has been partially expanded within the vessel. The ability to precisely control the relative movement of the components of the medical device delivery assembly is critical.

In accordance with an aspect of at least some embodiments disclosed herein is the realization that a medical device delivery system can have a control mechanism that allows for precise control and movement of components of the system. For example, the control mechanism can be advantageously configured to enable a clinician to carefully permit expansion of a stent from a catheter or to recapture, collapse, withdraw, rotate or resheath a stent within a catheter after the stent has been at least partially expanded.

In some embodiments, the control mechanism can be configured to control the relative movement of two or more components. The control mechanism can be used to control the movement of a component of a delivery system, such as a core wire, a microcatheter, a sheath, and/or a catheter. The control mechanism can comprise one or more engagement devices that is coupled to a respective component of the delivery system.

For example, a stent delivery assembly can comprise an outermost catheter in which an inner core assembly is slidably received, and the inner core assembly can comprise a sheath that encloses a stent that is engaged by a retention mechanism, which can include a guide wire or a microcatheter. Such delivery assemblies are disclosed in co-pending U.S. patent application Ser. No. 12/751,997, filed on Mar. 31, 2010; Ser. No. 12/426,560, filed on Apr. 20, 2009; Ser. No. 11/136,395, filed May 25, 2005; Ser. No. 11/420,025, filed May 24, 2006; Ser. No. 11/420,027, filed May 24, 2006; Ser. No. 12/425,604, filed Apr. 17, 2009; Ser. No. 12/896,707, filed Oct. 1, 2010; Ser. No. 61/483,615, filed May 6, 2011; Ser. No. 61/615,183, filed Mar. 23, 2012; Ser. No. 61/753,533, titled Methods and Apparatus for Luminal Stenting, filed on Jan. 17, 2013 (reference HKN-02607, 080373-0370); Ser. No. 13/692,021, titled Methods and Apparatus for Luminal Stenting, filed on Dec. 3, 2012 (reference HKN-02608 (2), 080373-0377); and Ser. No. 13/664,547, titled Methods and Apparatus for Luminal Stenting, filed on Oct. 31, 2012 (reference HKN-02608 (3), 080373-0498); the entireties of each of which are incorporated herein by reference. In order to deliver a medical device, such as the stent of such systems, both the sheath and the retention mechanism of the core assembly can be advanced within the outermost catheter. When the core assembly has reached the target location, the outermost catheter can be withdrawn proximally relative to the core assembly. Thereafter, the control mechanism can be used to effectuate movement of the sheath relative to the retention mechanism. For example, the sheath can be proximally withdrawn relative to the retention mechanism in order to expose the stent. Once the stent is exposed and confirmed to be properly positioned, the control mechanism can used to actuate the retention mechanism and effectuate release of the stent at the target location.

A control mechanism for a stent delivery assembly can be provided that comprises an alignment base, a first engagement device, and a second engagement device. The alignment base can comprise a first port, a second port proximal to the first port, and a channel extending along a longitudinal axis between the first and second ports. The base can also comprise a pair of wings on opposing sides of the channel. The wings can extend outwardly from the base. The wings can be movable between a first position in which the channel is in a relaxed, closed configuration and a second position in which the channel is in a deflected, open configuration. The first engagement device can be attachable to the first port. The first engagement device can be used to engage a first component. The second engagement device can be attachable to the second port. The second engagement device can engage a second component. Further, the first and second engagement devices can be (i) removable from the first and second ports when the wings are moved to the second position and (ii) retained in the first and second ports when the wings are in the first position to allow the first and second components to be axially aligned along the longitudinal axis.

The control mechanism can be configured to allow the base to include a substantially tubular configuration. The base can comprise a resilient material.

The control mechanism can also be configured to allow the first port to be disposed at a first end of the base and to allow the second port to be disposed at a second end of the base. The wings can extend from the first end to the second end along opposing sides of the channel.

Further, the first port can comprise at least one alignment portion, and the first engagement device comprises at least one mating portion configured to be aligned with the alignment portion when the first engagement device is attached to the first port.

The first port can comprise a plurality of alignment portions configured to allow the first engagement device to be positioned at a plurality of axial positions relative to the base to adjust a spacing between the first and second engagement devices. The at least one alignment portion can comprise a recess, and the at least one mating portion can comprise a protrusion. The at least one alignment portion can comprise an annular recess, and the at least one mating portion can comprise an annular protrusion.

The first engagement device can comprise a first pin vise, and the second engagement device can comprise a second pin vise.

Additionally, some embodiments provide an apparatus for a stent delivery assembly. The apparatus can comprise a first engagement device and a coupling mechanism. The first engagement device can be used to engage a first component. The coupling mechanism can have a port and at least one wing. The port can be configured to releasably interconnect with the first engagement device. The at least one wing can be disposed adjacent to the port. The at least one wing being movable between a first position and a second position. In the first position, the port can be in a relaxed, closed configuration for retaining the first engagement device in the aligned configuration. In the second position, the port can be in a deflected, open configuration for permitting removal or placement of the first engagement device into the port.

The apparatus can also comprise a second engagement device for engaging a second component. The coupling mechanism can be configured to mount the first and second engagement devices in an aligned configuration along a longitudinal axis of the coupling mechanism.

The first and second components can be axially aligned along the longitudinal axis when in the aligned configuration. The coupling mechanism can comprise a channel extending along the longitudinal axis thereof, between the first and second engagement devices.

The coupling mechanism can also comprise a second port configured to releasably interconnect with the second engagement device. Additionally, when the at least one wing is in the first position, the second port can be in a relaxed, closed configuration for retaining the second engagement device in the second port in the aligned configuration. Further, when the at least one wing is moved to the second position, the second port can be in a deflected, open configuration to permit the second engagement device to be removed from or placed into the second port.

The apparatus can also include a channel, extending along the longitudinal axis, and a slot, extending along the longitudinal axis, configured to permit the second component to be inserted or removed from the channel.

The apparatus can be configured to allow the port to be disposed at a first end of the base and the second port to be disposed at a second end of the base. The at least one wing can comprise a pair of wings that each extend from the first end to the second end along opposing sides of the channel.

In any such embodiment, the wings can be separated by a slot. The slot can extend into and along the channel. The slot can be configured to permit the second component to be inserted or removed from the channel. The wings can be substantially flat. For example, the wings can both extend in a first plane.

Further, the at least one wing or wings can be configured to move between the first and second positions in a direction transverse to the longitudinal axis of the apparatus.

The stent delivery system can be operated using a method comprising the steps of: grasping a control mechanism having (i) a first engagement device coupled to a first component of the stent delivery system, (ii) a second engagement device coupled to a second component of the stent delivery system, (iii) a port, configured to releasably interconnect with the first engagement device, and (iv) a at least one wing disposed adjacent to the port; separating the first engagement device from the control mechanism by deflecting the at least one wing from (a) a first position in which the first engagement device is coupled to the port of the control mechanism, to (b) a second position in which the port is in a deflected, open configuration to allow the first engagement device to be removed from the port; and adjusting an axial spacing between the first and second engagement devices to operate the stent delivery system.

The method can comprise operating the delivery system in any of the matters discussed herein. For example, the separating can comprise deflecting the at least one wing in a direction transverse to a longitudinal axis of the control mechanism.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

DETAILED DESCRIPTION

Figure 1:
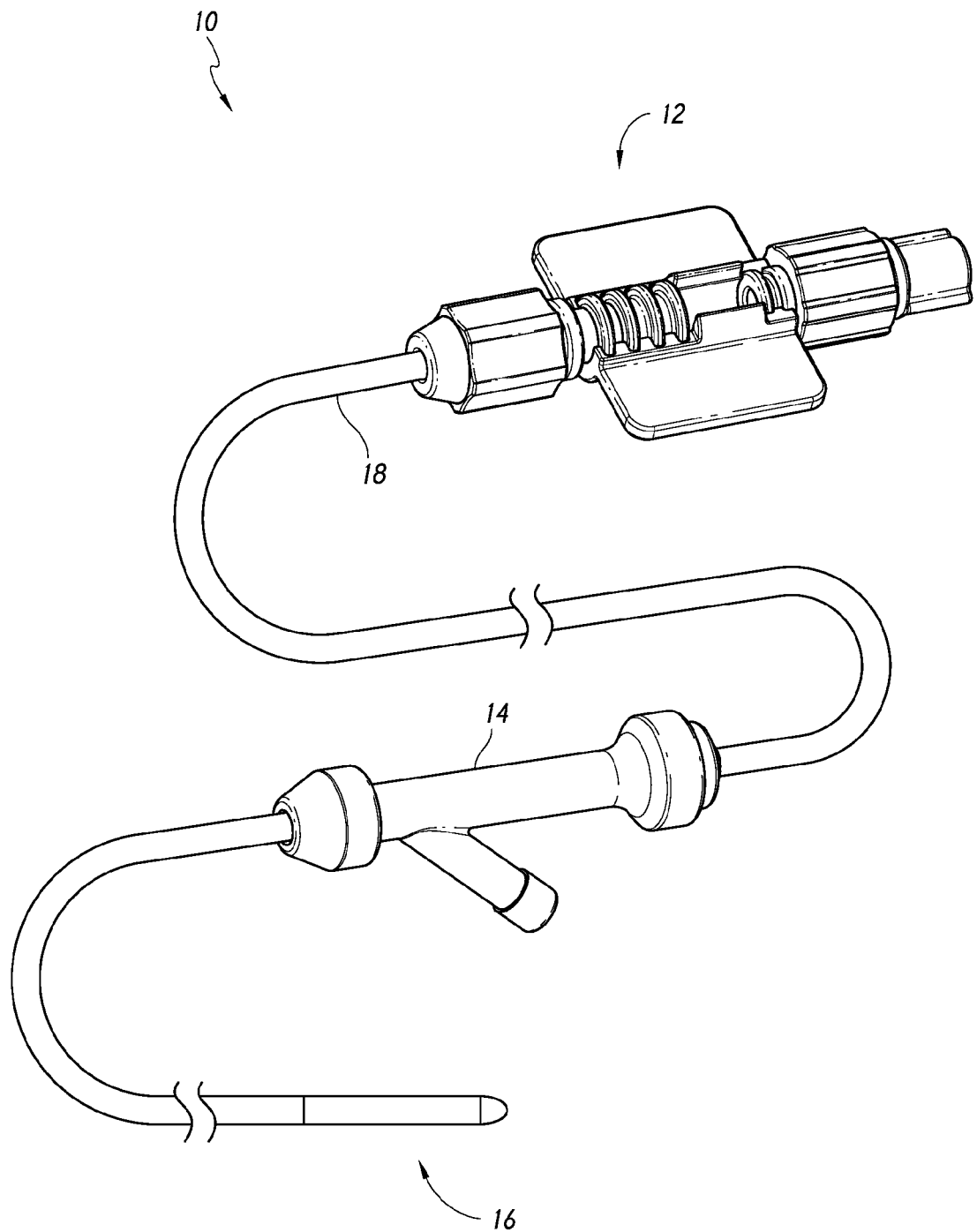
FIG. 1 is a schematic, perspective view of a medical device delivery system having a hemostatic valve and a deployment control mechanism, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Described herein are various embodiments of control mechanisms for use in medical device delivery systems exhibiting small cross-sections which are highly flexible and can provide advantages such as allowing the clinician to recapture, collapse, withdraw, or resheath and reposition a partially expanded medical device, avoid vessel abrasions or perforations during placement, place several medical devices (e.g., "telescoping" stents) without removing the microcatheter, and/or avoid torsional stress and "whipping" that can occur during delivery of the medical device. Various other features and advantages of embodiments are discussed and shown herein. Further, the delivery system and medical device used with embodiments of the control mechanisms can be made from various materials and comprise coatings or other features, such as those disclosed in co-pending U.S. patent application Ser. No. 13/692,021, titled Methods and Apparatus for Luminal Stenting, filed on Dec. 3, 2012 (reference HKN-02608 (2), 080373-0377), the entirety of which is incorporated herein by reference.

In some embodiments, a control mechanism is provided for a medical device delivery system that can include a core assembly and an introducer sheath and/or catheter. The control mechanism can comprise two or more engagement devices that are configured to be coupled to respective components of the delivery system. The engagement devices of the control mechanism can be used to precisely actuate the components of the delivery system when delivering the medical device.

The control mechanism can be configured to actuate various components of the medical device delivery system. For example, the core assembly can be actuated using the control mechanism to secure, grasp, or engage a portion of the medical device, such as a proximal end, to facilitate recapture, retraction, withdrawal, or resheathing of the medical device into the catheter lumen. In embodiments wherein the medical device is a stent, the stent can extend over, carried, or supported by a core member of the core assembly. The core member can comprise a core wire. The core assembly can be movable within the introducer sheath and/or catheter in order to deliver the stent to a predetermined treatment site, such as an aneurysm, within the vasculature of a patient. Thus, prior to delivery of the stent, the catheter can be configured to be introduced and advanced through the vasculature of the patient.

The core assembly can optionally comprise a constraining member or containment sheath, which can be actuated using the control mechanism. The core member of the core assembly can optionally comprise at least one protruding member or variable diameter portion disposed along the length of the core member that can cooperate with the constraining member or containment sheath to secure, grasp, or engage the stent in a press, friction, or interference fit. Accordingly, in some embodiments, the constraining member and the protruding member can cooperate to form a gripping mechanism that engages a proximal or first portion of the stent, and which can be actuated using the control mechanism. The gripping mechanism can secure or engage the first portion of the stent in a collapsed or expanded state.

For example, in some embodiments, a first engagement device of the control mechanism can be coupled to a containment sheath, and a second engagement device can be coupled to a core member of the core assembly. The first and second engagement devices can be movable relative to each other in order to move the containment sheath relative to the core member. The first and second engagement devices can also be coupled or fixed relative to each other using a holder or of the control mechanism. The holder can be a separate component from the first and second engagement devices, or it can be formed unitarily or of the same, continuous piece of material as the first or second engagement mechanisms.

Thus, the containment sheath and the core member can be advanced together within a lumen of a catheter toward a target site and when positioned at the target site, the first and second engagement devices can be decoupled in order to achieve relative movement between the containment sheath and the core member to permit expansion of the stent at the target site.

The control mechanism can be operated to allow the first and second engagement devices to be coupled together when an actuation device is in a first position and capable of being attached or detached relative to each other when the actuation device is in a second position. For example, the actuation device can comprise at least one wing that can be used to deflect or open at least one connection port of the mechanism for enabling attachment or removal of an engagement device relative to the other engagement device.

Indeed, after navigating the core assembly along the length of the catheter to the treatment site within the patient, the stent can be deployed from the catheter in a variety of ways. In one embodiment, the catheter can be retracted while maintaining the position of the core member to expose a distal end of the stent. While this is being done, the stent can be engaged in a collapsed state at least at the proximal end or portion thereof. In some embodiments, the stent can be engaged at both the proximal and distal ends or portions thereof while the catheter is being retracted. Further, the stent can be pinched, squeezed, or compressed between a pad of the core member and an inner wall of a containment sheath. Such embodiments are discussed and illustrated in co-pending U.S. patent application Ser. No. 13/692,021, titled Methods and Apparatus for Luminal Stenting, filed on Dec. 3, 2012 (reference HKN-02608 (2), 080373-0377), the entirety of which is incorporated herein by reference.

Additionally, in accordance with some embodiments, the control mechanism can be configured to allow the clinician can use the control mechanism to recapture, collapse, withdraw, or resheath the stent into the catheter and later deploy, expand or unsheath the stent again from the catheter after the stent has been partially expanded and even if the stent has been fully unsheathed or moved beyond a distal end of the catheter. As noted above, some embodiments allow the stent to be proximally secured, grasped, or engaged by the core assembly in order to both exert a distal pushing force on the stent and to exert a proximal pulling force on the stent. Thus, using the control mechanism, even when the stent has been fully unsheathed or moved beyond a distal end of the catheter, a proximal end of the stent can remain secured, grasped, or engaged with the core assembly to allow the stent to be retracted or withdrawn proximally into the catheter until the entire length of the stent has been resheathed into the catheter.

Some embodiments of the control mechanism can be configured to allow a clinician to rotate components of the delivery system that are coupled to the control mechanism. For example, the control mechanism can be used with a stent delivery system that includes a steerable tip mechanism or steerable tip assembly. The steerable tip mechanism can comprise a steerable wire having a curvilinear distal end that can allow a clinician to avoid abrading or perforating the vessel wall during the procedure. A first engagement mechanism of the control mechanism can be coupled to the steerable wire and a second engagement mechanism of the core assembly can be coupled to a sheath or other such component of the stent delivery system. The first engagement mechanism can be rotated relative to the second engagement mechanism in order to induce rotation of the wire relative to the sheath and/or stent to permit the clinician to avoid abrasion or perforation of the blood vessel or to avoid dislodging the stent from the vessel wall after initial expansion of the stent.

Therefore, if the treatment site is adjacent to a tortuous vessel location (e.g., a sharp turn in the vessel) or a bifurcation, for example, the control mechanism can allow the clinician to select or control the direction in which the core member extends in order to avoid abrasions or perforations of the vessel during expansion and delivery of the stent at the treatment site.

Features of Control Mechanisms

FIGS. 1-8 depict embodiments of a control mechanism for a medical device delivery system which may be used to deliver and/or deploy a stent into a hollow anatomical structure such as a blood vessel. Various medical devices, such as stents, and delivery system components, such as catheters, sheaths, core wires, and the like can be used with the control mechanism. For example, information regarding components of the delivery system, such as stents or catheters used in the delivery system, and additional details and components that can optionally be used or implemented with some embodiments of the control mechanism described herein, can be found in U.S. Patent Application Publication No. 2011/0238041 A1, published on Sep. 29, 2011, titled Variable Flexibility Catheter, or U.S. patent application Ser. No. 13/692,021, titled Methods and Apparatus for Luminal Stenting, filed on Dec. 3, 2012 (reference HKN-02608 (2), 080373-0377), the entireties of which are hereby incorporated by reference herein and made a part of this specification.

FIG. 1 illustrates an embodiment of a medical device delivery assembly 10 having a control mechanism 12, a hemostatic valve 14, and a medical device delivery portion 16. The delivery assembly 10 can also comprise one or more components, such as one or more catheters or sheaths 18, one or more core wires or members, and/or other components.

The assembly 10 can be used to deliver a variety of medical devices, including stents, occlusion devices, filters, valves, and other such intravascular devices.

Figure 2:
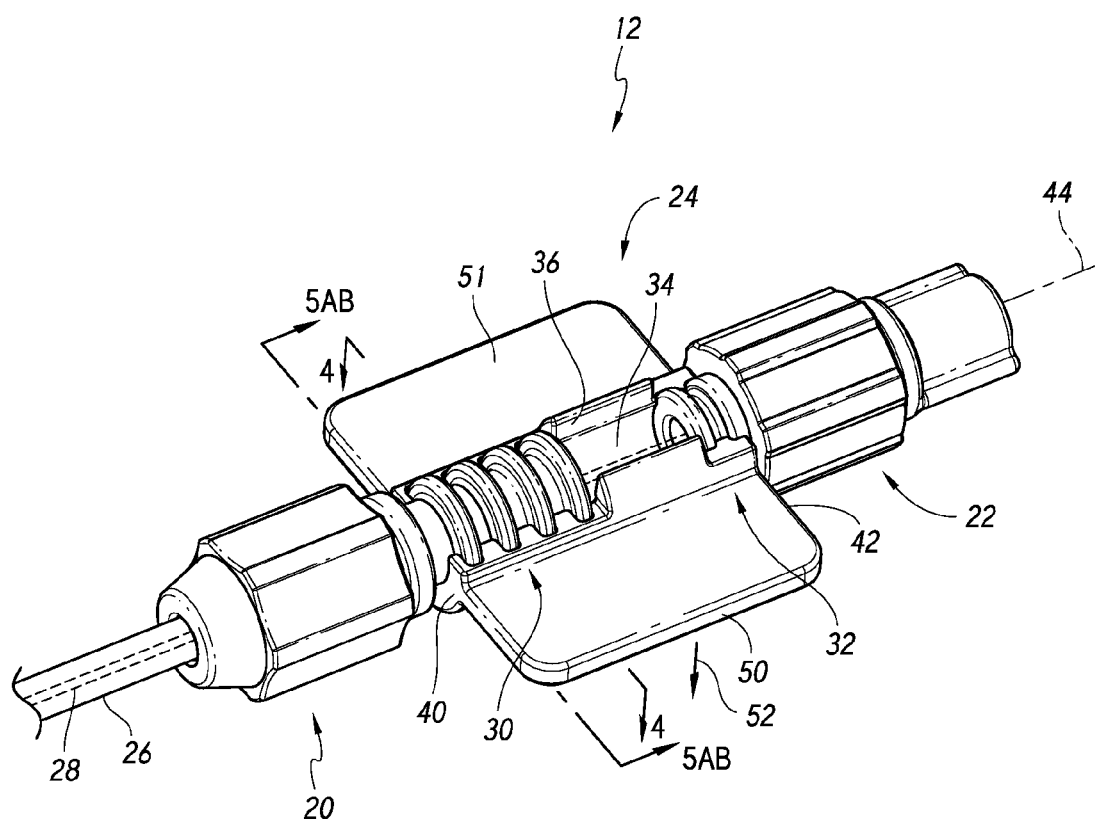
FIG. 2 is a perspective view of a control mechanism, according to some embodiments.

FIG. 2 illustrates a perspective view of an embodiment of the control mechanism 12. As shown, the control mechanism 12 can comprise a first engagement device 20, a second engagement device 22, and a base 24. The first engagement device 20 and the second engagement device 22 can both be coupled to a respective component of the delivery assembly 10. As shown in FIG. 2, the first engagement device 20 can be coupled to a sheath or catheter 26, and the second engagement device 22 can be coupled to a core member or wire 28.

According to some embodiments, the base 24 and the second engagement device 22 can be formed separately from each other and be removably interconnectable. Further, the first engagement device 20 can be removably interconnectble with the base 24.

The base 24 can comprise a coupling mechanism for mounting or interconnecting the first and second engagement devices 20, 22 relative to each other. For example, the coupling mechanism can be configured to allow the base 24 to include a first port 30 and a second port 32 that is positioned proximal to the first port 30 relative to a clinician's point of view. Additionally, the base 24 can also comprise a channel 34 extending between the first and second ports 30, 32.

The first and second ports 30, 32 can be located at respective first and second ends 40, 42 of the base 24. The first and second ports 30, 32 can be configured to receive at least a portion of the respective ones of the first and second engagement devices 20, 22 for coupling the first and second engagement devices 20, 22 relative to each other. As illustrated, the first and second engagement devices 20, 22 can be generally aligned along the channel 34, which is aligned along a longitudinal axis 44 of the control mechanism 12, in an aligned configuration.

The coupling mechanism can also comprise at least one actuation device that is configured to facilitate engagement or disengagement between the first and second engagement devices 20, 22, and in some embodiments, between the first and second engagement devices 20, 22 and the base 24. The base 24 can comprise a substantially tubular configuration. Further, the base 24 can comprise a resilient material. Thus, the base 24 can be deflected to increase or decrease the size of the lumen or opening of the base 24 (and/or the port(s) 30, 32 thereof), thereby permitting engagement or disengagement with at least the first engagement device 20, and in some embodiments, both the first and second engagement devices 20, 22.

For example, the coupling mechanism can include at least one button or wing 50 of the base 24. In the embodiment illustrated in FIG. 2, the base 24 comprises a pair of wings 50, 51; however, a single wing 50 can be used to actuate the coupling mechanism, according to some embodiments. The wing 50 can be movable between first and second positions that allow the mechanism 12 to engage with or release at least one of the engagement devices. In embodiments in which the second engagement device 22 is formed unitarily with the base 24 (e.g., being formed of a single, continuous piece of material), the wing 50 can be used to actuate open and closed positions of the first port 30. For example, in an open position, the first port 30 can be configured to allow entry or exit of a portion of the first engagement device 22 from the first port 30. In a closed position, the first port 30 can securely engage with, collapse around, or otherwise restrict movement of a portion of the first engagement device 22 disposed within the first port 30.

Additionally, in embodiments in which the base 24 is formed separately from the first and second engagement devices 20, 22, the wing 50 can be configured to actuate open and closed positions of the first and second ports 30, 32. Similar to the manner described above, the wing 50 can be actuated to allow the first and second ports 30, 32 to be opened to receive or release a portion of the respective first or second engagement device 20, 22, or closed to securely engage with, collapse around, or otherwise restrict movement of a portion of the first or second engagement device 20, 22 disposed within the first or second port 30, 32.

The embodiment of FIG. 2 is illustrated as having a pair of wings 50, 51 that extend continuously from the first end 40 to the second end 42 of the base 24. The wings 50, 51 extend on opposing sides of the channel 34. The channel 34 can comprise a slot 36 that separates the wings 50, 51 and extends into the channel 34. The slot 36 can be configured to allow the first engagement device 20, and in some embodiments, the second engagement device 22, to be inserted or removed from the channel 34. As shown, in some embodiments, the slot 36 can extend continuously from the first port 30 to the second port 32. However, the slot 36 can also be discontinuous or broken.

However, some embodiments can be configured to allow the first port 30 to be paired with at least one distal wing and the second port 32 is paired with at least one proximal wing that is separate from the distal wing. The distal and proximal wings can be configured to actuate the first and second ports 30, 32 independently of each other, thereby providing additional control and precision for the clinician.

Figure 5A:
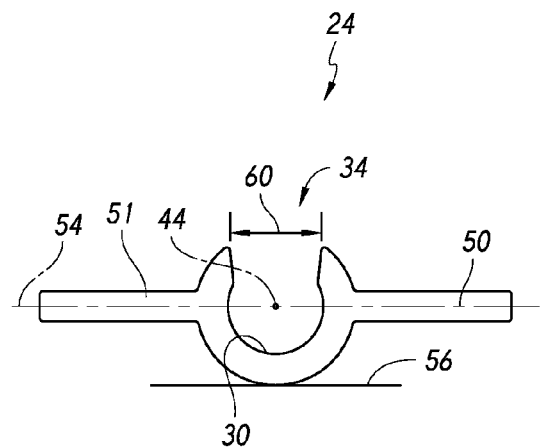
FIG. 5A is an end, partial cross-sectional view of the control mechanism shown in FIG. 2, wherein a base of the control mechanism is in an unstressed configuration, according to some embodiments.
Figure 5B:
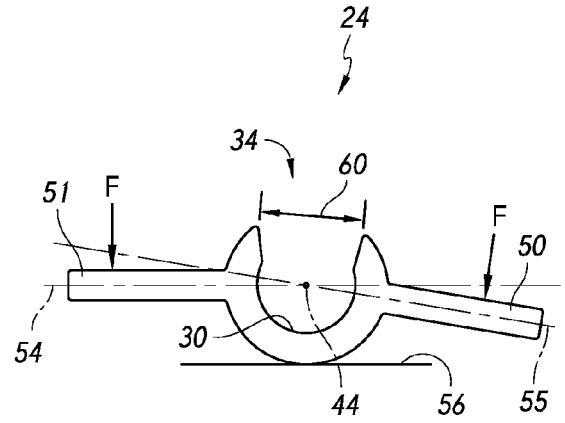
FIG. 5B is an end, partial cross-sectional view of the control mechanism shown in FIG. 2, wherein a base of the control mechanism is in a stressed or deformed configuration, according to some embodiments.

FIG. 2 also illustrates that according to some embodiments, the wing 50 can be moved in a direction 52 that is transverse relative to the longitudinal axis 44 of the control mechanism 12. With reference to FIGS. 5A-B, which illustrate and views of the control mechanism 12 taken along section lines 5AB-5AB of FIG. 2, the base 24 of the control mechanism 12 is shown, placed on a surface 56 (for illustrative purposes only), in a relaxed, closed configuration for retaining the first engagement device 20 in the first port 30 (FIG. 5A) and in a deflected, open configuration for permitting removal or placement of the first engagement device 20 into the first port 30.

FIG. 5A illustrates that in the relaxed, closed configuration, a width 60 of the channel 34 (or of either or both ports 30, 32) assumes a first value. However, in FIG. 5B, after a force, F, is exerted on the wing 50, the width 60 of the channel 34 (or port(s) 30, 32) is urged to a second value that is greater than the first value. Accordingly, the exertion of a force, F, on the wing 50 can increase the width 60 of the channel 34 and/or port(s) 30, 32, thus allowing additional clearance for placement of a structure, such as a portion of the first engagement device 20, into the first port 30. The operation and use of the wing 50 for the first port 30 can be the same as the second port 32 or similarly implemented at the second port 32 using a separate wing for independent actuation of the second port 32.

As illustrated in FIGS. 5A-5B, the base 24 can comprise a pair of wings 50, 51. The wings 50, 51 can be substantially flat. Further, the wings 50, 51 can both extend in a first plane 54. When deflected, the wings 50, 51 can then be in different planes 54, 55, as shown in FIG. 5B, e.g. by virtue of one or both wings 50, 51 deflecting relative to the surface 56, the base 24 and/or each other.

Figure 6A:
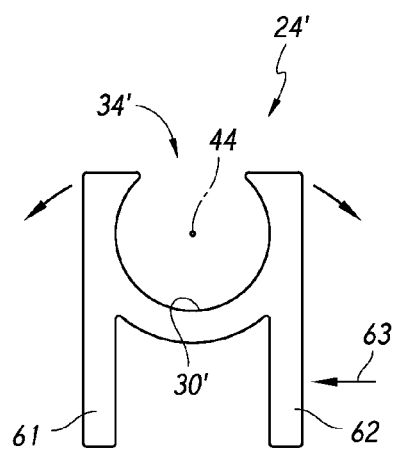
FIG. 6A is an end, partial cross-sectional view of a control mechanism, according to some embodiments.
Figure 6B:
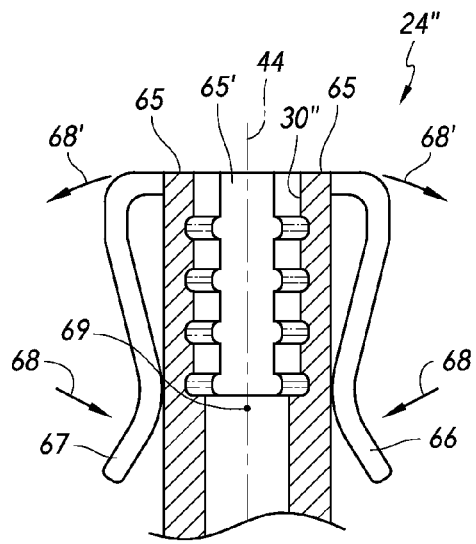
FIG. 6B is a cross-sectional top view of a control mechanism, according to some embodiments.

FIGS. 6A-6B illustrate additional features of embodiments of a coupling mechanism. FIG. 6A is a cross-sectional end view of a coupling mechanism (taken of another embodiment from an angle similar to the view of FIG. 5A). As illustrated in FIG. 6A, the coupling mechanism can comprise one or more wings 61, 62 that are oriented generally parallel relative to each other. The wings 60, 61 can be actuated or deflected in a direction 63 that is generally transverse relative to the longitudinal axis 44 in order to increase the width of the channel 34' of the base 24'. Accordingly, the embodiment of FIG. 6A can operate similarly to the embodiment shown in FIGS. 5A-5B in that the wings 61, 62 and 50, 51 can be actuated to open or increase clearance into or out of a port 30, 30' of the base 24, 24' by creating a moment about an axis generally parallel to the longitudinal axis 44.

Figure 4:
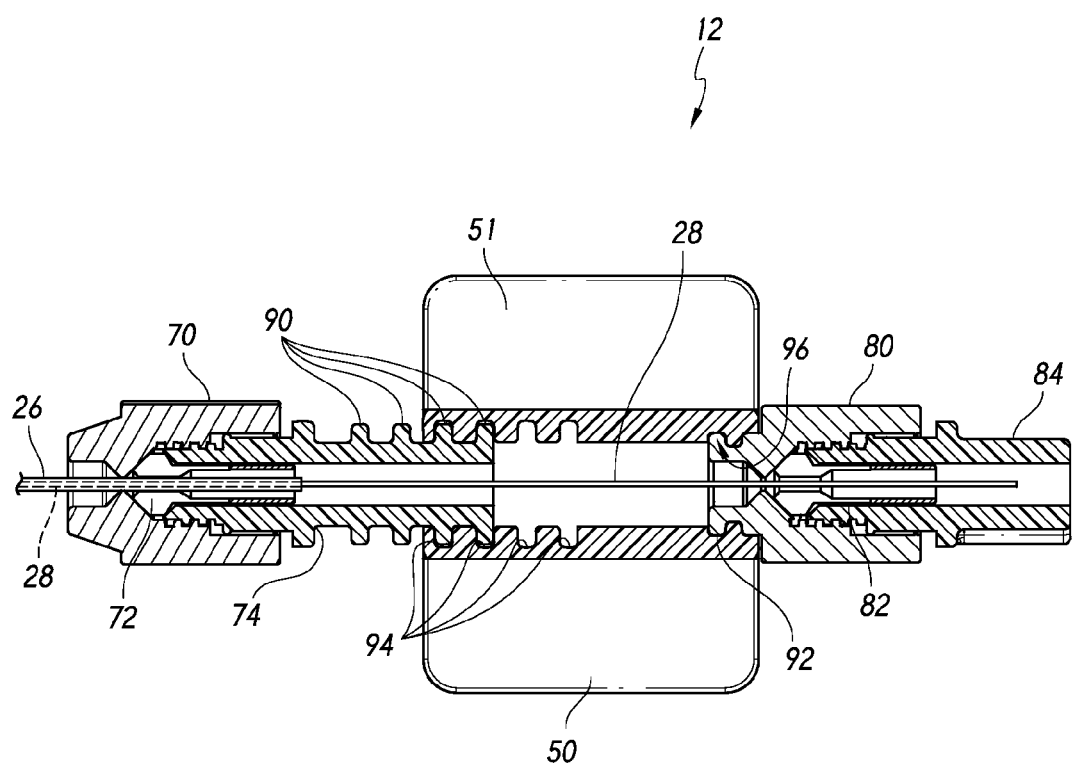
FIG. 4 is a top, cross-sectional view of the control mechanism shown in FIG. 2, according to some embodiments.

However, in other embodiments, such as that illustrated in FIG. 6B (which is a cross-sectional, top view, taken of another embodiment from an angle similar to the view of FIG. 4), the coupling mechanism of a base 24" can comprise one or more wings 66, 67 that can be actuated using a force 68 to open or increase clearance into or out of a port 30" by creating a moment about an axis 69 that is generally transverse to the longitudinal axis 44. Thus, the embodiment of FIG. 6B illustrates an embodiment in which the wings 66, 67 can be pinched together toward the longitudinal axis 44 of the base 24". This motion can cause end portions 62 to move radially apart from each other. For example, the end portions 65 can be formed or separated by a lower slot 65' and an upper slot (not shown), that allow the end portions 65 to move apart from each other generally in the direction illustrated by the arrows 68', creating a moment that is transverse to the longitudinal axis 44.

Figure 3:
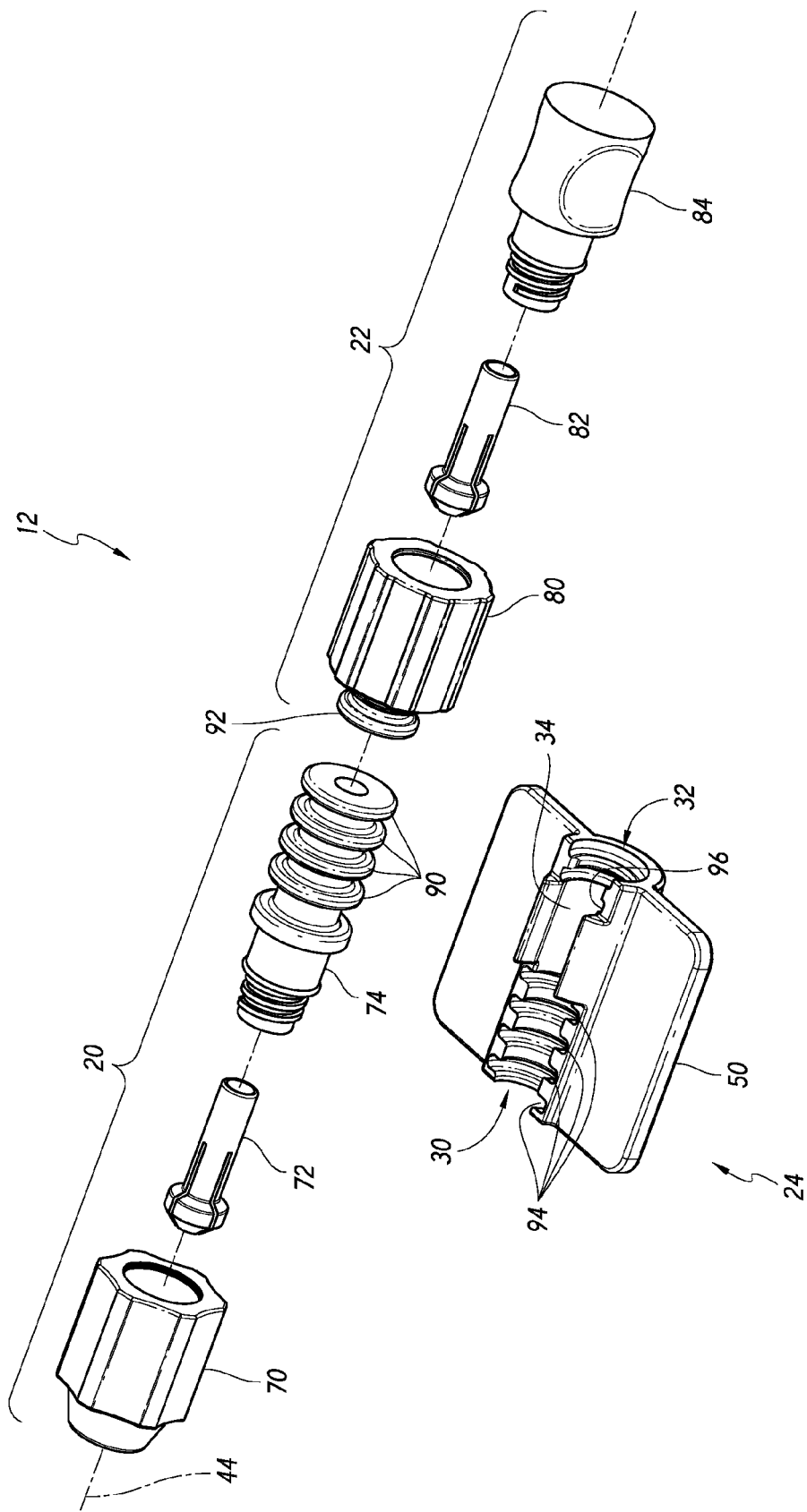
FIG. 3 is an exploded view of the control mechanism shown in FIG. 2, according to some embodiments.

Referring now to FIG. 3, an embodiment of the control mechanism 12 is shown in an exploded configuration. Further, FIG. 4 illustrates a top, cross-sectional view of the control mechanism 12. As shown, the control mechanism 12 can comprise first and second engagement devices 20, 22 in the form of individual, interconnectable components that facilitate gripping of or engagement with the components of the delivery system, particularly a core member thereof such as a core wire or hypotube. For example, the first engagement device 20 can comprise a pin vise and the second engagement device 22 can comprise a pin vise.

According to some embodiments, the first engagement device 20 can comprise a distal hub or nut 70, a distal collet 72, and a distal body 74. The second engagement device 22 can comprise a proximal hub or nut 80, a proximal collet 82, and a proximal body 84. Both the first and second engagement devices 20, 22 can operate similarly to the each other in engaging a component of the delivery system. In particular, as with collet-type devices, the component (e.g., a sheath, catheter, or a core member such as a hypotube or wire), can be inserted through a lumen of the hub and into a lumen of the collet. The collet can then be placed into a lumen of the body and the body can be inserted into the lumen of the hub. Thereafter, by threaded engagement, the hub can be tightened onto the body, with the collet disposed therein, which causes inwardly deflectable arms of the collet to deflect inward and tighten around the component inserted into the collet lumen.

FIGS. 3-4 also illustrates that the first and second engagement devices 20, 22 can comprise one or more structures configured to engage with the base 24. For example, the distal body 74 and the proximal hub 80 can each comprise at least one structure configured to engage with (e.g., to be received by or to receive) a corresponding structure of the base 24.

The first and second engagement devices 20, 22 can be engaged with the base 24 in only one axial spacing or position. However, some embodiments can be configured to allow the first and/or second engagement devices 20, 22 to be coupled to the base 24 in a plurality of axial spacings or positions.

As illustrated, the distal body 74 and the proximal hub 80 can comprise one or more mating portions 90, 92. Although FIGS. 3-4 illustrate four mating portions 90 and a single mating portion 92, the distal body 74 and the proximal hub 80 can each comprise one, two, three, five, six, seven, eight, nine, ten, or more individual mating portions. Each mating portion 90, 92 can comprise a protrusion and/or a recess. Each mating portion 90, 92 can extend fully or partially around the entire perimeter of the distal body 74 or proximal hub 80 in a continuous or discontinuous manner.

For example, FIGS. 3-4 illustrate that each mating portion 90, 92 extends continuously around the entire perimeter of the distal body 74 or proximal hub 80 to form an annular protrusion. Further, the distal body 74 or proximal hub 80 can be configured to allow the mating portions 90, 92 to extend generally transverse to the longitudinal axis 44. However, the distal body 74 or proximal hub 80 can also comprise one or more portions (e.g., a protrusion or recess) that extend generally parallel relative to the longitudinal axis 44, which can be useful to maintain a rotational alignment between the distal body 74 or proximal hub 80 and the ports 30, 32 of the base 24.

Further, FIGS. 3-4 also illustrate that the first and second ports 30, 32 can comprise at least one alignment portion 94, 96. Although FIGS. 3-4 illustrate four alignment portions 94 and a single alignment portion 96, the first and second ports 30, 32 can each comprise one, two, three, four, five, six, seven, eight, nine, ten, or more individual alignment portions. Each alignment portion 94, 96 can comprise a protrusion and/or a recess. Each alignment portion 94, 96 can extend fully or partially around the internal surface of the channel 34 of the base 24. In one or both ports 30, 32, the alignment portions can be longitudinally separated from each other by a uniform longitudinal separation distance, in order to facilitate movement of the engagement device(s) 20, 22 longitudinally relative to the base, and reattachment thereto in a new position that is longitudinally separated from the previous position by the separation distance or a multiple thereof.

In accordance with some embodiments, at least one alignment portion and/or at least one mating portion can comprise a deflectable, resilient material or otherwise be configured to mechanically deflect so as to provide a longitudinal alignment mechanism that allows an engagement device to be axially translated along a series of discrete longitudinal positions relative to the base or other engagement device. The ratcheting mechanism can enable the clinician to incrementally draw the first and second engagement devices together, by distance(s) set by the spacing of the alignment portion(s) 94, 96, during stent deployment and expansion. Additionally, the alignment mechanism facilitates convergence of the engagement devices and an off-axis motion to enable the clinician to separate or otherwise adjust the axial spacing or position of the engagement devices.

Accordingly, by adjusting the axial spacing and interconnecting selected ones of the mating portions and alignment portions, some embodiments can allow the first and/or second engagement devices 20, 22 to be coupled to the base 24 in a plurality of axial spacings or positions. The illustrated embodiment of FIGS. 3-4 illustrates that the first port 30 comprises four alignment portions 94 (shown as annular recesses) that can be interconnected or engaged with four mating portions 90 (shown as annular protrusions) of the distal body 74. Such an embodiment with thus allow four axial spacings or positions between the base 24 and the first engagement device 20.

A similar effect and number of axial spacings or positions can be achieved when the structural arrangements are reversed: the first port 30 can comprise a single alignment portion and the distal body 74 can comprise a plurality of mating portions, which can result in the same number of axial spacings or positions. More or fewer alignment portions and mating portions can be used to affect the number of potential axial spacings or positions and/or the stability of the interconnection.

Figure 7A:
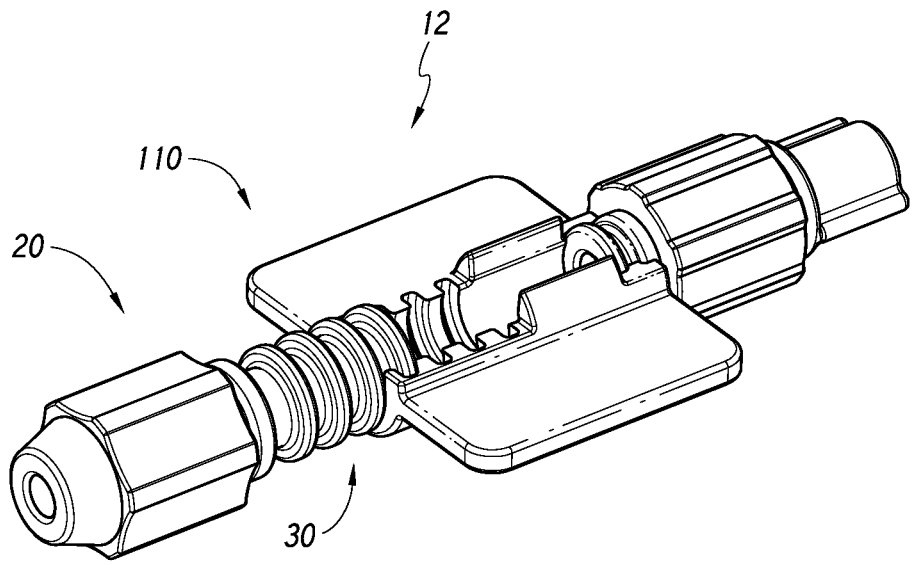
FIGS. 7A-7D are perspective views of a control mechanism wherein components of the control mechanism are shown in different operating positions, according to some embodiments.
Figure 7B:
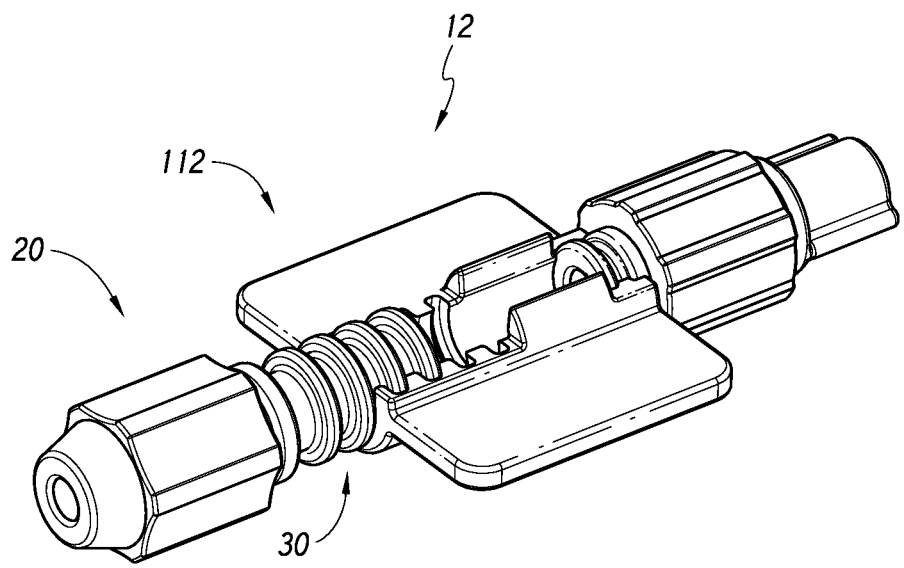
Figure 7C:
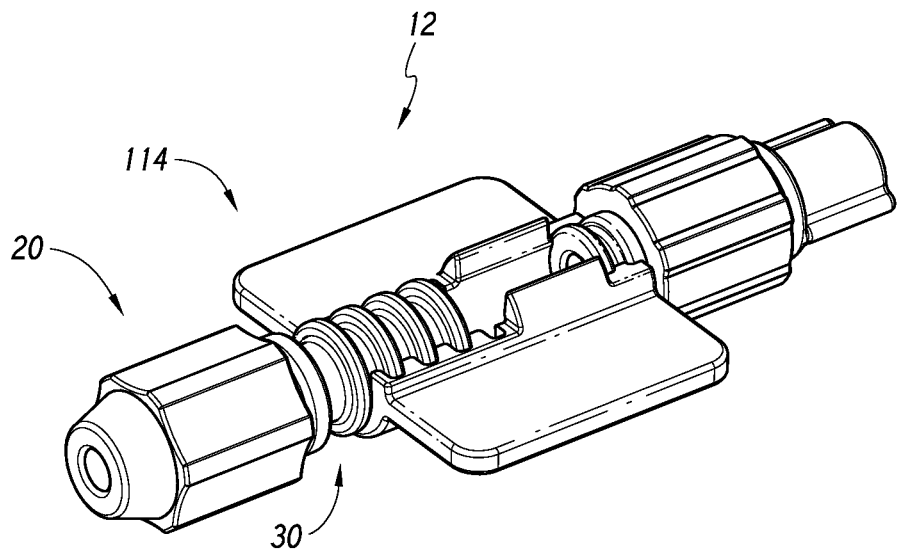
Figure 7D:
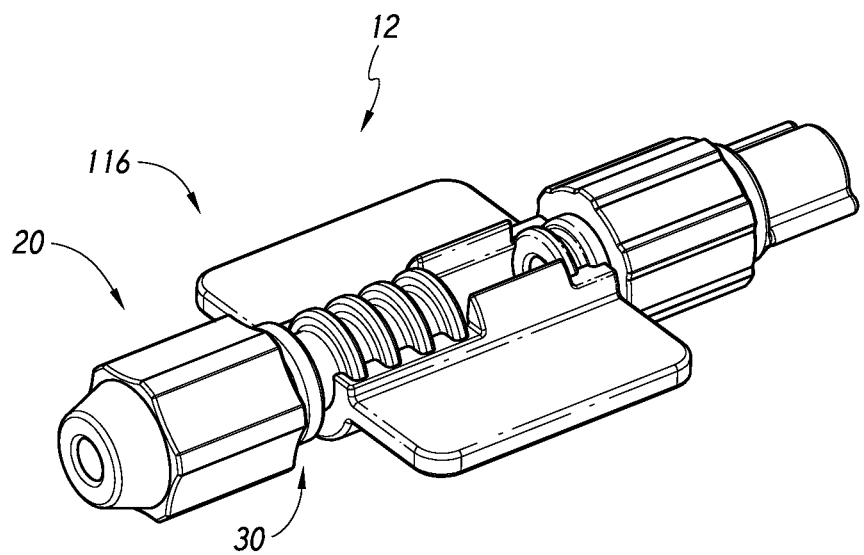

FIGS. 7A-7D illustrate the control mechanism 12 in four different axial spacings or positions. FIG. 7A shows the first engagement device 20 at a first position 110, in which a single annular mating portion is interconnected with a single alignment portion of the first port 30. FIG. 7B shows the first engagement device 20 at a second position 112, in which two annular mating portions are interconnected with two alignment portions of the first port 30. FIG. 7C shows the first engagement device 20 at a third position 114, in which three annular mating portions are interconnected with three alignment portions of the first port 30. FIG. 7D shows the first engagement device 20 at a fourth position 116, in which four annular mating portions are interconnected with four alignment portions of the first port 30.

Further, although discussed with respect to the first engagement device 20, the same principles can be used with regard to the second engagement device 22 in embodiments in which the second engagement device 22 is separate from the base 24.

As noted above, the control mechanism can be configured to allow a clinician to independently rotate one or more components of the delivery system. Accordingly, one or both of the engagement devices can be rotated relative to each other and/or the base of the control mechanism. This is true of the control mechanism 12, and its engagement devices 20, 22, which can be independently rotated with respect to each other and the base 24, when attached thereto via the ports 30, 32. Such rotational capability can be used when one of the components of a stent delivery system must be rotated relative to the other, for example when employing a stent delivery system in which a component can be rotated to release the stent. For this reason, the control mechanisms disclosed herein, including the control mechanisms 12 and 200, may be employed with the occluding device delivery assemblies disclosed in U.S. Pat. No. 8,236,042, the entirety of which is hereby incorporated by reference herein. For example, the engagement device 22 may be coupled to a proximal portion of the guidewire 21 of the aforementioned U.S. Pat. No. 8,236,042 and the engagement device 20 may be coupled to the micro-catheter 1 thereof. The engagement device 22 can therefore be rotated to rotate the guidewire 21 and protective coil 35 of the '042 patent relative to the occluding device 100 and micro-catheter thereof, and release the distal end of the occluding device.

Figure 8:
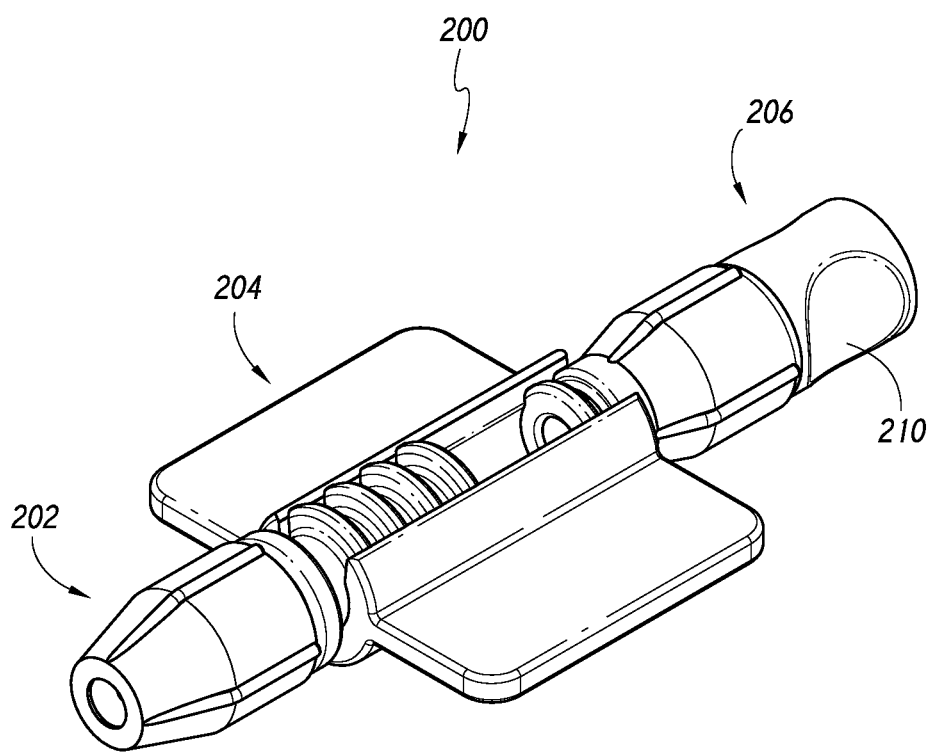
FIG. 8 is a perspective view of another control mechanism, according to some embodiments.

FIG. 8 illustrates another embodiment of a control mechanism 200 which can be similar in structure, function and method of use to the control mechanism 12, and contain further variations thereof as described herein. As illustrated, the control mechanism 200 can include a first engagement device 202, a base 204, and a second engagement device 206. The second engagement device 206 can comprise a handle section 210 that can be configured to facilitate gripping and rotation by the clinician. Other such features and structures for facilitating actuation of the coupling mechanism, rotation of one or more engagement devices of the control mechanism, or overall manipulate ability or handling of the control mechanism can be implemented.

Methods of Using the Control Mechanism

FIGS. 9-13 depict some embodiments and methods of use of a stent delivery system 290, which can incorporate or employ any of the various embodiments of the control mechanism disclosed herein, including the control mechanisms 12 and 200. First, a catheter 300 can be inserted into a lumen 302 of a blood vessel 304 via a percutaneous access technique or other suitable method of access. A distal end of the catheter 300 is then advanced to a treatment site or location in the blood vessel 304. The blood vessel 304 may comprise a vein or artery, such as an artery in a brain or within a cranium of the patient. The catheter 300 can comprise a microcatheter. A guide catheter can be used instead of or in addition to the catheter 300; for example, the guide catheter can first be placed in the vasculature so that it extends part or all of the way to the treatment site and a microcatheter or other catheter then inserted through the guide catheter to the treatment site.

The treatment location may be near an aneurysm 306 formed in a wall of the blood vessel 304, and advancing the catheter 300 to the treatment location may include advancing a distal end and/or distal opening 308 of the catheter 300 to a location that is distal of the aneurysm 306. Such advancement of the catheter 300 may include advancing the distal end and/or distal opening 308 distally across the ostium or neck of the aneurysm, to the location in the vessel 304 distal of the aneurysm 306.

Once the catheter 300 has been inserted, it may extend proximally from the distal end and/or distal opening 308 at the treatment location, through the vascular access site, to a proximal end and/or hub which are preferably situated outside the patient's body.

After the catheter 300 has been placed, a core assembly 320 (having, e.g., a containment sheath, cover member or sheath 322, a stent 324, and a core member 326) can be inserted, distal end first, into the lumen of the catheter 300 via the hub and/or proximal end. In the illustrated embodiment of the core assembly 320, the containment sheath 322 can be configured to withstand a radially outward force of a radially protruding member 330, 332 that radially squeezes, pinches, compresses, or engages the stent 324 between the protruding member 330, 332 and an inner surface or wall of the cover member or sheath 322. In addition, the depicted containment sheath 322 extends over and covers the entire length of the stent 324, and is employed to release both the distal and proximal ends of the stent during deployment; alternatively, the containment sheath 322 can extend over and cover only the proximal end of the stent 324 during delivery through the catheter 300, and then be used to release only the proximal end during deployment, once the catheter 300 has been withdrawn to expose and deploy the distal end.

Figure 9:
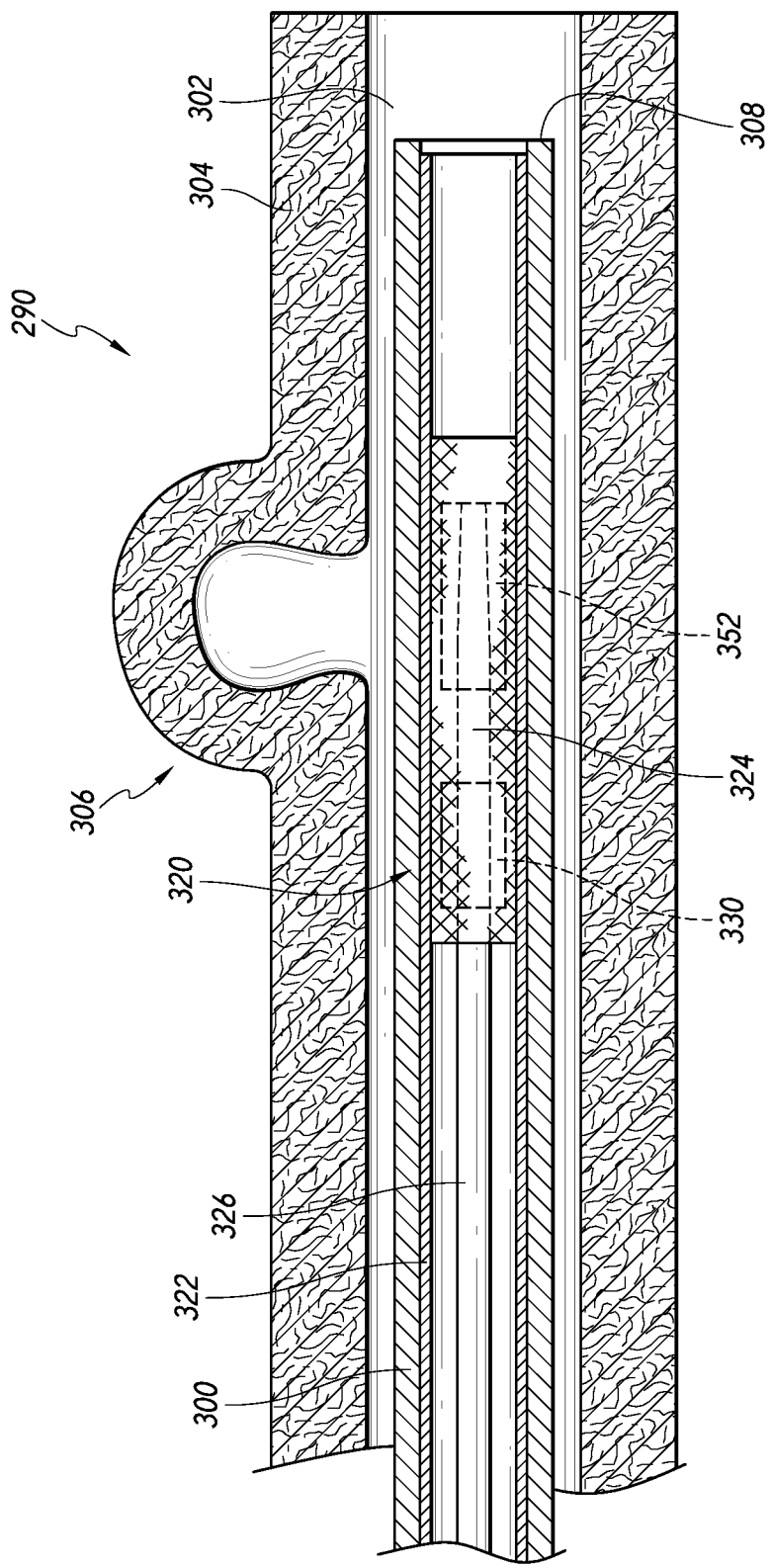
FIG. 9 is a schematic, partial cross-sectional view of a medical device delivery system, according to an embodiment.

In the control mechanism, the first engagement device (e.g., the first engagement device 20 or 202) can be coupled to the sheath 322 and the second engagement device (e.g., the second engagement device 22 or 206) can be coupled to the core member 326. Where the distal portion of the core assembly 320 is initially contained within an introducer sheath (not shown), the introducer sheath can be inserted partway into the catheter lumen and the core assembly 320 can be advanced distally through the introducer sheath until the containment sheath 322 and the stent 324 exit the distal end of the introducer sheath and pass into the lumen of the catheter 300. The first and second engagement devices 20, 22 of the control mechanism can fixed relative to each other, in an interconnected configuration, such as by being coupled together using the base 24 of the control mechanism, to allow the containment sheath 322 and stent 324 to be advanced together in an axially-fixed manner through the lumen of the catheter 300 until reaching the target site, as shown in FIG. 9.

Figure 10:
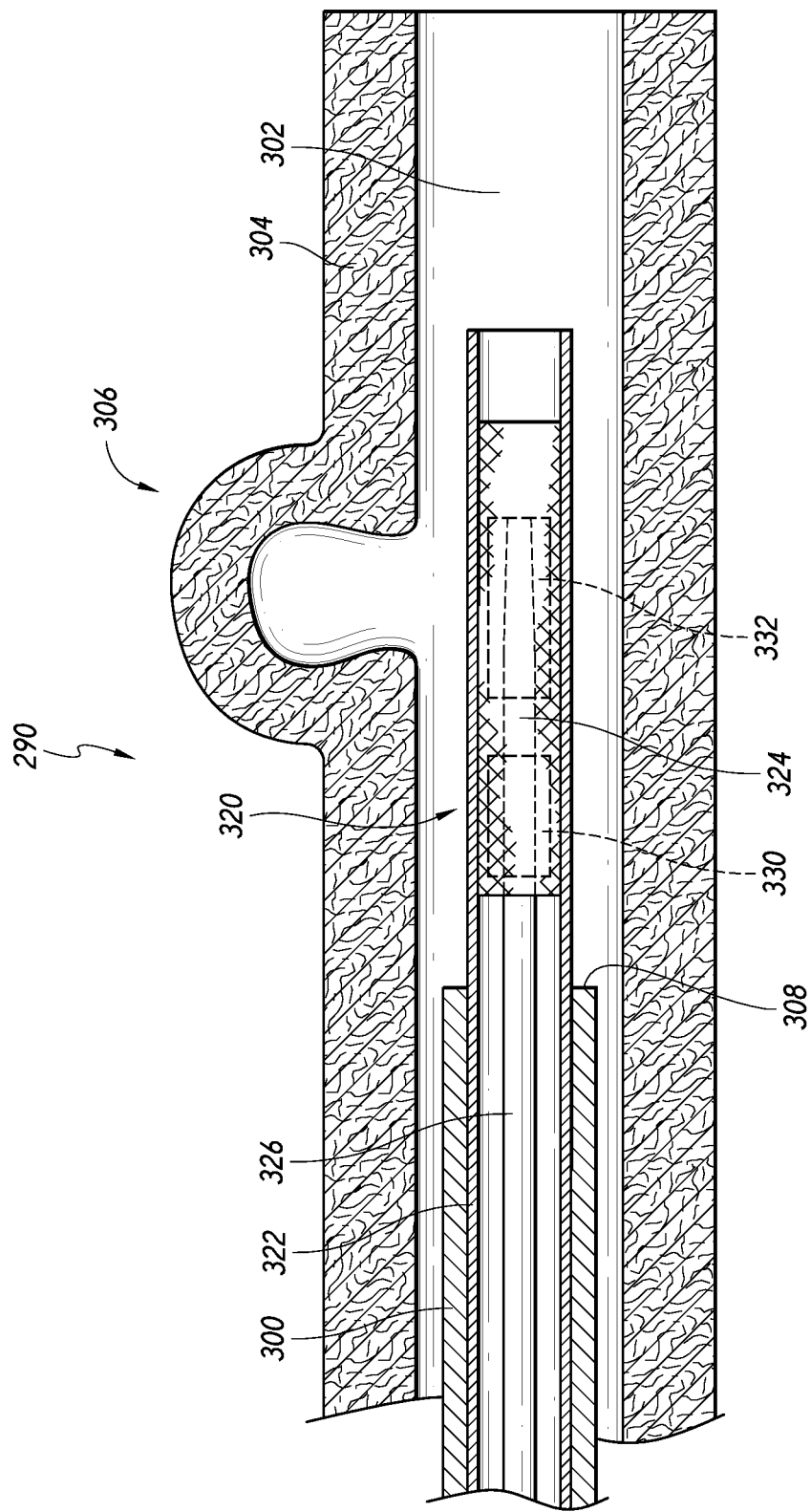
FIG. 10 is a schematic, partial cross-sectional view of the system of FIG. 9, in which a catheter has been retracted relative to a sheath thereof, according to some embodiments.

In order to begin deployment and expansion of the stent 324, the catheter 300 can be withdrawn proximally until the distal end 308 of the catheter 300 is positioned proximal to the stent 324, as shown in FIG. 10. During proximal withdrawal of the catheter 300, the control mechanism can be maintained in the interconnected configuration so as to maintain the containment sheath 322 and the stent 324 in a fixed axial relationship.

Figure 11:
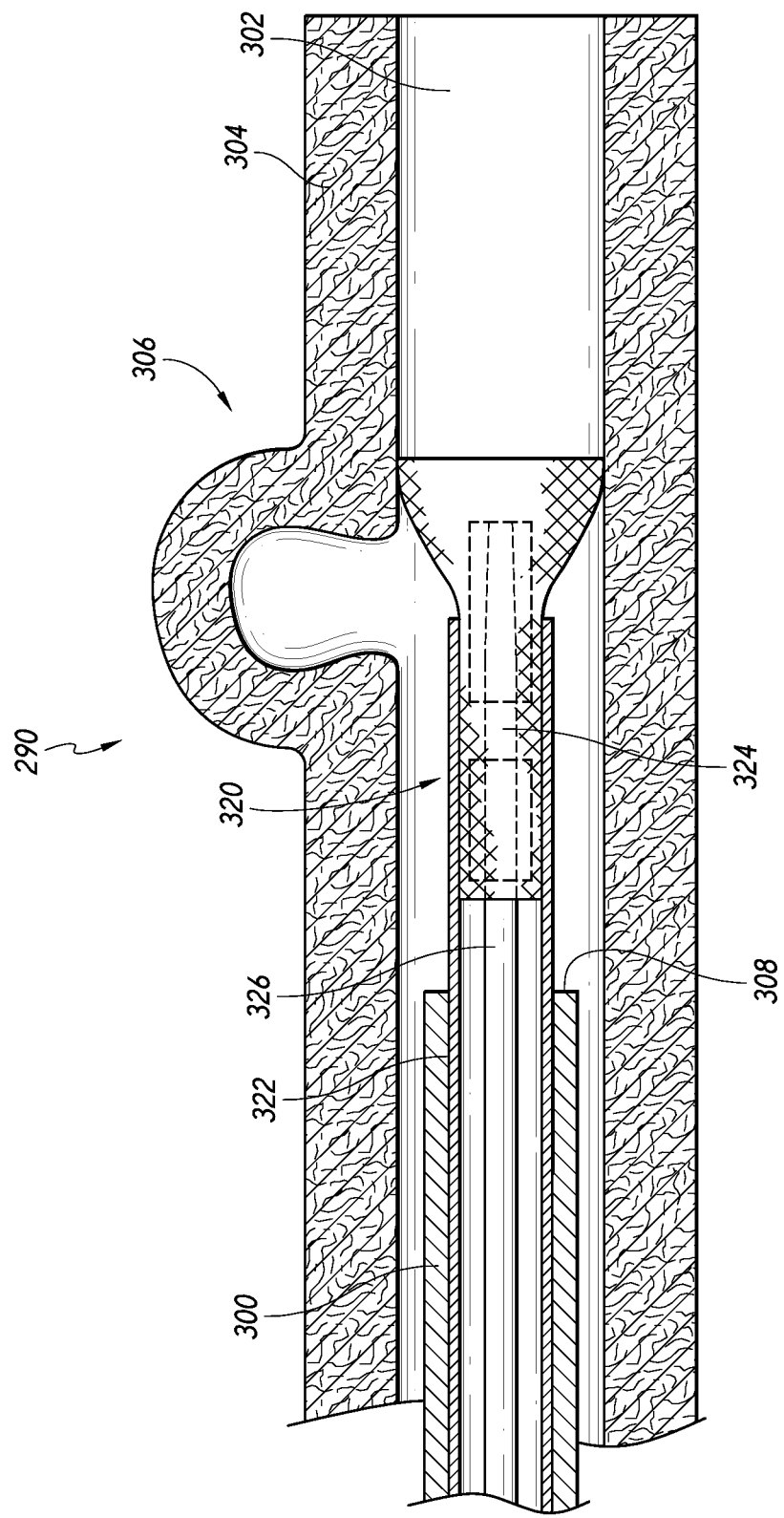
FIG. 11 is a schematic, partial cross-sectional view of the system of FIG. 9, in which the sheath has been partially retracted relative to a stent thereof to permit initial expansion of the stent, according to some embodiments.

After the catheter 300 has been withdrawn, the control mechanism can be actuated by withdrawing the first engagement device proximally relative to the second engagement device, thereby retracting the containment sheath 322 relative to the stent somewhat and producing an initial stent expansion, as shown in FIG. 11. In doing so, the mating portion of the first or second engagement device can be decoupled from the first or second port and the first and/or second engagement devices can be moved toward each other and fixed in the base in the new, closer arrangement.

According to some embodiments, and as discussed above, the engagement devices can be separated from each other by deflecting a wing of the control mechanism from (a) a first position in which the engagement device coupled to the port of the control mechanism, to (b) a second position in which the port is in a deflected, open configuration to allow the engagement device to be removed from the port. Thereafter, and axial spacing between the engagement devices can be adjusted in order to operate the delivery system. Any of the various control mechanisms disclosed herein can be used. As such, the deflection can occur in the direction of the longitudinal axis of the control mechanism or in a direction transverse to the longitudinal axis.

Figure 12:
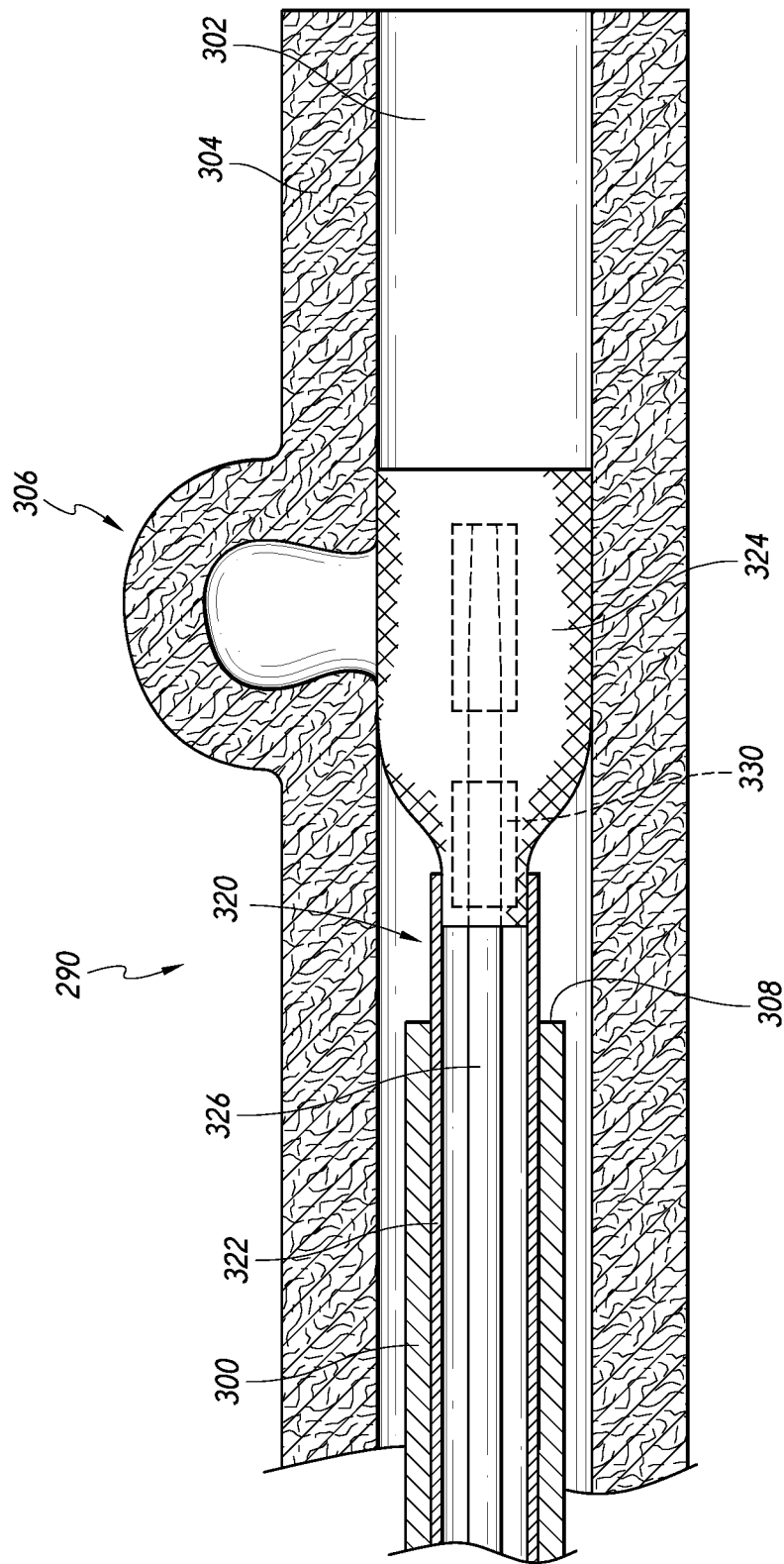
FIG. 12 is a schematic, partial cross-sectional view of the system of FIG. 9, in which the sheath has been further retracted relative to the stent to permit additional expansion of the stent, according to some embodiments.
Figure 13:
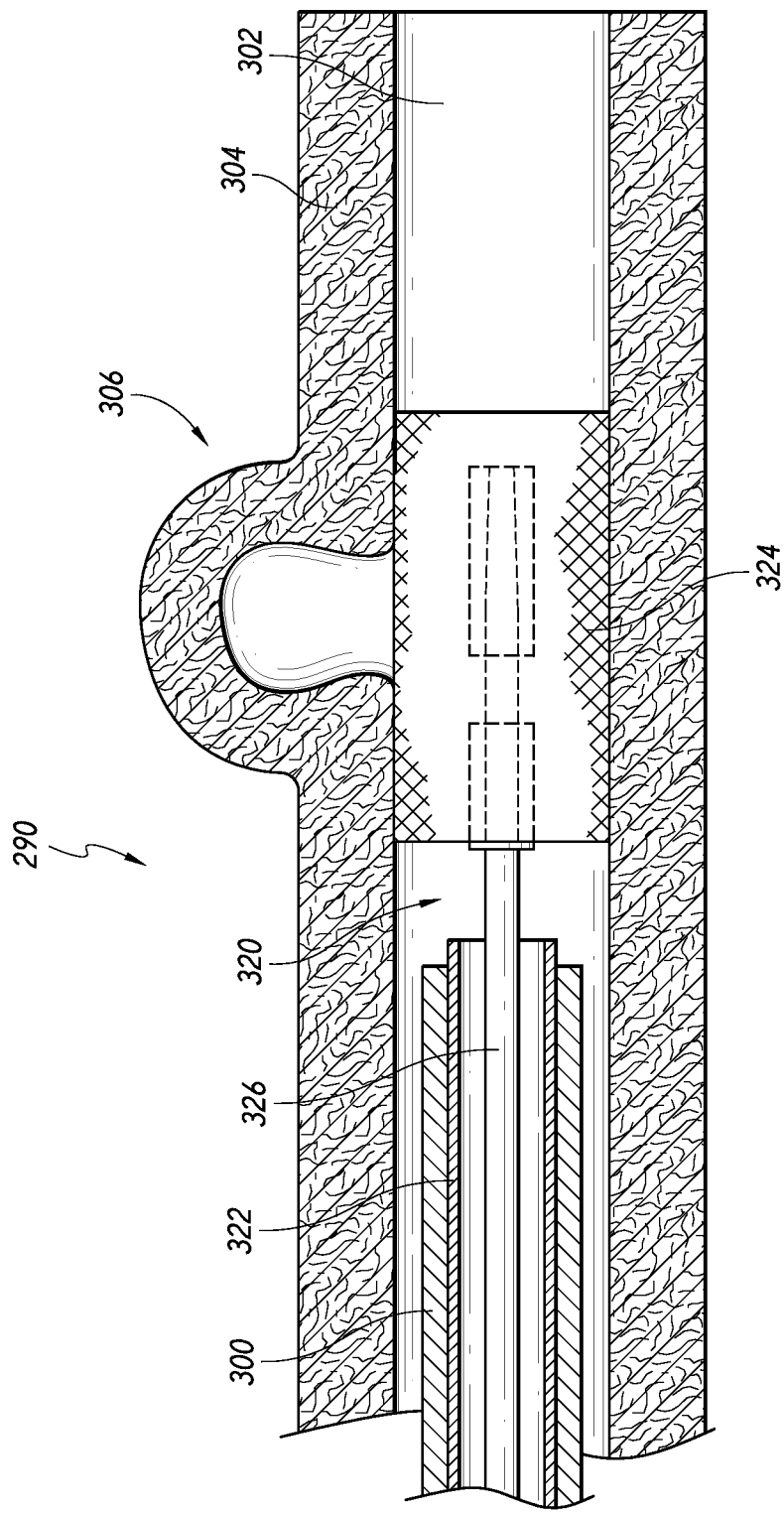
FIG. 13 is a schematic, partial cross-sectional view of the system of FIG. 9, in which the sheath has been fully retracted relative to a stent to permit full expansion of the stent, according to some embodiments.

For example, the first engagement device shown in FIG. 7A can be moved from the first position 110 to the second position 112 shown in FIG. 7B. As the clinician verifies the initial placement and expansion of the stent 324, the first and second engagement devices can be further moved from the second position 112 to the third position 114 shown in FIG. 7C to produce the movement and further expansion of the stent, as illustrated in FIG. 12. Thereafter, should the deployment and expansion of the stent 324 be acceptable, the clinician can move the first and second engagement devices to a fourth position 116, shown in FIG. 7D to allow the stent to be fully released and expanded into apposition with the blood vessel 304, as shown in FIG. 13.

During placement and verification of expansion of the stent 324, the clinician can survey the surrounding vasculature of the treatment site and determine whether there is a risk of having the distal end of the core member abrade or perforate a vessel wall as the core member is advanced distally as anticipated during stent expansion or during advancement of the system to the treatment location. If necessary, the clinician can also rotate one or both of the first and second engagement devices of the control mechanism in order to steer components of the core assembly in order to avoid abrasion or perforation of the vessel wall.

Following full expansion of the stent 324, the core assembly 320 can be drawn back into the catheter 300, as shown in FIG. 12. Both the catheter 300 and core assembly 320 can be withdrawn from the patient, either simultaneously or sequentially. However, when the stent has been successfully released, the core assembly 320 can also be entirely removed from the catheter 300, with the catheter 300 remaining in place, and a second core assembly can be inserted into the lumen. The second core assembly can be configured to deliver a second stent to the treatment site in order to perform, e.g., a telescoping procedure in which two stents are deployed in an end-to-end fashion, with the distal end of a first stent received in the proximal end of a second stent.

In another embodiment of a method, the stent 324 can be initially partially expanded (e.g., as shown in FIG. 11) in a blood vessel 304 wherein a branch vessel (not shown) joins the blood vessel at a junction located along the portion of the vessel 304 in which the stent 324 has been partially expanded. Patency of the branch vessel can then be checked by, for example, injecting a contrast agent near the junction and observing via, for example, fluoroscopy whether the agent can flow from the vessel 304 into the branch vessel. Thus it can be determined whether a portion of the stent 324 has occluded the branch vessel. If it appears that the branch vessel has been occluded, the stent 324 can be repositioned within the vessel 304 without resheathing, or the stent 324 can be resheathed using any of the techniques discussed herein. After resheathing, the stent 324 can be partially expanded again, and branch vessel patency checked again.

In the present disclosure, numerous references are made to moving the catheter 300 axially over the core assembly 320, and moving the core assembly 320 axially within the catheter 300. Further, numerous references are made to moving the first engagement device proximally toward the second engagement device and moving the second engagement device distally toward the first engagement device. For movement of the catheter and core assembly and the first and second engagement devices, except where specifically noted to the contrary, all such references to one form of this relative movement should be understood to include the other as an alternative.

Information regarding additional embodiments of the stent delivery system 100, 1000, and additional details and components that can optionally be used or implemented in the embodiments of the stent delivery system described herein, can be found in the above-incorporated U.S. Patent Application Publications Nos. US 2011/0152998 A1 and US 2009/0318947A1. The stent delivery system 100 disclosed herein can optionally be similar to any of the delivery systems disclosed in these publications, except as further described herein.

The apparatus and methods discussed herein are not limited to the expansion and use of an stent or occluding device within any particular vessels, but may include any number of different types of vessels. For example, in some aspects, vessels may include arteries or veins. The vessels may have bifurcations and/or sharp turns. In some aspects, the vessels may be suprathoracic vessels (e.g., vessels in the neck or above), intrathoracic vessels (e.g., vessels in the thorax), subthoracic vessels (e.g., vessels in the abdominal area or below), lateral thoracic vessels (e.g., vessels to the sides of the thorax such as vessels in the shoulder area and beyond), or other types of vessels and/or branches thereof.

In some aspects, the suprathoracic vessels may comprise at least one of intracranial vessels, cerebral arteries, and/or any branches thereof. For example, the suprathoracic vessels may comprise at least one of a common carotid artery, an internal carotid artery, an external carotid artery, a middle meningeal artery, superficial temporal arteries, an occipital artery, a lacrimal (ophthalmic) artery, an accessory meningeal artery, an anterior ethmoidal artery, a posterior ethmoidal artery, a maxillary artery, a posterior auricular artery, an ascending pharyngeal artery, a vertebral artery, a left middle meningeal artery, a posterior cerebral artery, a superior cerebellar artery, a basilar artery, a left internal acoustic (labyrinthine) artery, an anterior inferior cerebellar artery, a left ascending pharyngeal artery, a posterior inferior cerebellar artery, a deep cervical artery, a highest intercostal artery, a costocervical trunk, a subclavian artery, a middle cerebral artery, an anterior cerebral artery, an anterior communicating artery, an ophthalmic artery, a posterior communicating artery, a facial artery, a lingual artery, a superior laryngeal artery, a superior thyroid artery, an ascending cervical artery, an inferior thyroid artery, a thyrocervical trunk, an internal thoracic artery, and/or any branches thereof. The suprathoracic vessels may also comprise at least one of a medial orbitofrontal artery, a recurrent artery (of Heubner), medial and lateral lenticulostriate arteries, a lateral orbitofrontal artery, an ascending frontal (candelabra) artery, an anterior choroidal artery, pontine arteries, an internal acoustic (labyrinthine) artery, an anterior spinal artery, a posterior spinal artery, a posterior medial choroidal artery, a posterior lateral choroidal artery, and/or branches thereof. The suprathoracic vessels may also comprise at least one of perforating arteries, a hypothalamic artery, lenticulostriate arteries, a superior hypophyseal artery, an inferior hypophyseal artery, an anterior thalamostriate artery, a posterior thalamostriate artery, and/or branches thereof. The suprathoracic vessels may also comprise at least one of a precentral (pre-Rolandic) and central (Rolandic) arteries, anterior and posterior parietal arteries, an angular artery, temporal arteries (anterior, middle and posterior), a paracentral artery, a pericallosal artery, a callosomarginal artery, a frontopolar artery, a precuneal artery, a parietooccipital artery, a calcarine artery, an inferior vermian artery, and/or branches thereof.

In some aspects, the suprathoracic vessels may also comprise at least one of diploic veins, an emissary vein, a cerebral vein, a middle meningeal vein, superficial temporal veins, a frontal diploic vein, an anterior temporal diploic vein, a parietal emissary vein, a posterior temporal diploic vein, an occipital emissary vein, an occipital diploic vein, a mastoid emissary vein, a superior cerebral vein, efferent hypophyseal veins, infundibulum (pituitary stalk) and long hypophyseal portal veins, and/or branches thereof.

The intrathoracic vessels may comprise the aorta or branches thereof. For example, the intrathoracic vessels may comprise at least one of an ascending aorta, a descending aorta, an arch of the aorta, and/or branches thereof. The descending aorta may comprise at least one of a thoracic aorta, an abdominal aorta, and/or any branches thereof. The intrathoracic vessels may also comprise at least one of a subclavian artery, an internal thoracic artery, a pericardiacophrenic artery, a right pulmonary artery, a right coronary artery, a brachiocephalic trunk, a pulmonary trunk, a left pulmonary artery, an anterior interventricular artery, and/or branches thereof. The intrathoracic vessels may also comprise at least one of an inferior thyroid artery, a thyrocervical trunk, a vertebral artery, a right bronchial artery, a superior left bronchial artery, an inferior left bronchial artery, aortic esophageal arteries, and/or branches thereof.

In some aspects, the intrathoracic vessels may also comprise at least one of a right internal jugular vein, a right brachiocephalic vein, a subclavian vein, an internal thoracic vein, a pericardiacophrenic vein, a superior vena cava, a right superior pulmonary vein, a left brachiocephalic vein, a left internal jugular vein, a left superior pulmonary vein, an inferior thyroid vein, an external jugular vein, a vertebral vein, a right highest intercostal vein, a 6th right intercostal vein, an azygos vein, an inferior vena cava, a left highest intercostal vein, an accessory hemiazygos vein, a hemiazygos vein, and/or branches thereof.

In some aspects, the subthoracic vessels may comprise at least one of renal arteries, inferior phrenic arteries, a celiac trunk with common hepatic, left gastric and splenic arteries, superior suprarenal arteries, a middle suprarenal artery, an inferior suprarenal artery, a right renal artery, a subcostal artery, 1st to 4th right lumbar arteries, common iliac arteries, an iliolumbar artery, an internal iliac artery, lateral sacral arteries, an external iliac artery, a testicular (ovarian) artery, an ascending branch of deep circumclex iliac artery, a superficial circumflex iliac artery, an inferior epigastric artery, a superficial epigastric artery, a femoral artery, a ductus deferens and testicular artery, a superficial external pudendal artery, a deep external pudendal artery, and/or branches thereof. The subthoracic vessels may also comprise at least one of a superior mesenteric artery, a left renal artery, an abdominal aorta, an inferior mesenteric artery, colic arteries, sigmoid arteries, a superior rectal artery, 5th lumbar arteries, a middle sacral artery, a superior gluteal artery, umbilical and superior vesical arteries, an obturator artery, an inferior vesical and artery to ductus deferens, a middle rectal artery, an internal pudendal artery, an inferior gluteal artery, a cremasteric, pubic (obturator anastomotic) branches of inferior epigastric artery, a left colic artery, rectal arteries, and/or branches thereof.

In some aspects, the lateral thoracic vessels may comprise at least one of humeral arteries, a transverse cervical artery, a suprascapular artery, a dorsal scapular artery, and/or branches thereof. The lateral thoracic vessels may also comprise at least one of an anterior circumflex humeral artery, a posterior circumflex humeral artery, a subscapular artery, a circumflex scapular artery, a brachial artery, a thoracodorsal artery, a lateral thoracic artery, an inferior thyroid artery, a thyrocervical trunk, a subclavian artery, a superior thoracic artery, a thoracoacromial artery, and/or branches thereof.

In some embodiments, the delivery system 100 can include an expandable occluding device (e.g., stent 324) configured to be placed across an aneurysm. The occluding device can be delivered through the distal portion of the catheter, out a distal tip assembly, and into the vasculature adjacent an aneurysm in, for example, the middle cerebral artery. A proximal portion of the catheter can remain partially or entirely within a guiding catheter during delivery, and an intermediate portion, taper portion, and distal portion of the catheter can extend distally of the guiding catheter. The occluding device can be released at the target location and can be used to occlude blood flow into the aneurysm. The catheter can be used to reach target locations (e.g., aneurysms) located elsewhere in the body as well, include but not limited to other arteries, branches, and blood vessels such as those described above.

Various examples of aspects of the subject technology are described as numbered clauses (1, 2, 3, etc.) for convenience. These are provided as examples, and do not limit the subject technology. It is noted that any of the dependent clauses may be combined in any combination, and placed into a respective independent clause, e.g., clause 1 and 21. The other clauses can be presented in a similar manner.

The apparatus and methods discussed herein are not limited to the deployment and use of an occluding device or stent within the vascular system but may include any number of further treatment applications. Other treatment sites may include areas or regions of the body such as organ bodies.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed within the scope of the disclosure.

What is claimed is:

1. A control mechanism for a stent delivery assembly, comprising:
   an alignment base comprising a first port, a second port proximal to the first port, and a channel extending along a longitudinal axis between the first and second ports, the base further comprising a pair of wings, on opposing sides of the channel, extending outwardly from the base, the wings being movable between a first position in which the channel is in a relaxed, closed configuration and a second position in which the channel is in a deflected, open configuration;

a first engagement device, couplable to the first port, for engaging a first component, wherein when coupled to the first port, the first engagement device is (i) permitted to rotate about the longitudinal axis without causing the first engagement device to move along the longitudinal axis and (ii) restricted from moving along the longitudinal axis relative to the first port; and a second engagement device, couplable to the second port, for engaging a second component, wherein when coupled to the second port, the second engagement device is (i) permitted to rotate about the longitudinal axis without causing the second engagement device to move along the longitudinal axis and (ii) restricted from moving along the longitudinal axis relative to the second port, wherein the first and second engagement devices are (i) removable from the first and second ports when the wings are moved to the second position and (ii) retained in the first and second ports when the wings are in the first position to allow the first and second components to be axially aligned along the longitudinal axis.

2. The control mechanism of claim 1, wherein the wings are separated by a slot, extending into and along the channel, configured to permit the second component to be inserted or removed from the channel.

3. The control mechanism of claim 1, wherein the wings both extend in a first plane.

4. The control mechanism of claim 1, wherein the first port is disposed at a first end of the base, and the second port is disposed at a second end of the base, and each of the wings extends from the first end to the second end along opposing sides of the channel.

5. The control mechanism of claim 1, wherein the first port comprises at least one alignment portion, and the first engagement device comprises at least one mating portion configured to be aligned with the alignment portion when the first engagement device is coupled to the first port.

6. The control mechanism of claim 5, wherein the first port comprises a plurality of alignment portions configured to allow the first engagement device to be positioned at a plurality of axial positions relative to the base to adjust a spacing between the first and second engagement devices.

7. The control mechanism of claim 5, wherein the at least one alignment portion comprises a recess, and the at least one mating portion comprises a protrusion.

8. The control mechanism of claim 7, wherein the at least one alignment portion comprises an annular recess, and the at least one mating portion comprises an annular protrusion.

9. The control mechanism of claim 1, wherein the wings move between the first and second positions in a direction transverse to the longitudinal axis.

* * * * *